United States Patent [19]

Kaiser

[11] 4,169,676

[45] Oct. 2, 1979

[54] METHOD FOR DETERMINING THE CONTENTS OF METABOLIC PRODUCTS IN THE BLOOD

[76] Inventor: Nils Kaiser, Germeringer Str. 36, Gauting, Fed. Rep. of Germany

[21] Appl. No.: 769,777

[22] Filed: Feb. 17, 1977

[30] Foreign Application Priority Data

Feb. 20, 1976 [DE] Fed. Rep. of Germany ....... 2606991

[51] Int. Cl.² ............................................ G01N 33/16
[52] U.S. Cl. .................................... 356/39; 23/230 R; 23/230 B; 422/68; 128/630
[58] Field of Search ........................ 23/230 B, 230 R; 250/341; 356/39; 128/2 A

[56] References Cited

U.S. PATENT DOCUMENTS

| 3,308,709 | 3/1967 | Harrick | 350/96 R |
| 3,313,290 | 4/1967 | Chance et al. | 128/2 A |
| 3,803,384 | 4/1974 | Braunlich | 250/345 |

OTHER PUBLICATIONS

Malone et al., Spectrochimica Acta, 21, 1361 (1963).

Primary Examiner—Michael S. Marcus
Attorney, Agent, or Firm—Finnegan, Henderson, Farabow & Garrett

[57] ABSTRACT

A method and instrument for determining the amounts of metabolic products in blood using a laser beam guided through an ATR plate placed against a blood supplied biological tissue. The intensity of the beam is then detected after being affected by the blood containing the metabolic elements and is used to determine the amounts of metabolic products in the blood.

9 Claims, 5 Drawing Figures

METHOD FOR DETERMINING THE CONTENTS OF METABOLIC PRODUCTS IN THE BLOOD

BACKGROUND OF THE INVENTION

The invention relates to an instrument for determining the amounts of metabolic products in the blood by means of a radiation source and a radiation detection system delivering an output signal depending on the intensity of radiation of the aforesaid source after it has been affected by the blood containing the metabolic products.

Generally, the determination of amounts of metabolic products such as polypeptises, urea, cholesterol, glucose, $CO_2$ or ethyl alcohol in the blood is carried out by withdrawing blood from the body and examining it chemically. However, the time required for ascertaining the particular amounts is relatively long and ranges from a few minutes to an hour.

On the one hand, there is danger in such extended periods of time that the blood may alter resulting in spurious results. On the other hand, a continuous testing of the metabolic products, as is desirable for instance when examining the glucose content when suspecting diabetes, or when determining the $CO_2$ content during artificial respiration in the course of an operation, is impossible. Again, it is impossible, in current techniques, to ascertain transiently occurring, unknown metabolic products.

It is furthermore known that the metabolic products in the blood absorb infrared (IR) radiation, so that they may be ascertained by means of absorption measurements. However, such infrared absorption tests suffer from the difficulty that the blood acting as a solvent for the metabolic products in itself represents an aqueous solution which is strongly absorbing in the infrared spectrum, as is well known. Therefore, when performing measurements by means of previously known IR spectrometers on the basis of transmission, very minute film thicknesses are required to obtain measurement signals that are useful at all. This requires in turn that the dissolved substances to be tested must be present at very high concentrations so that a relative change in absorption can be detected at all. Therefore only concentrations exceeding 1 percent can be ascertained in fact when using previously known IR spectrometers.

As shown by the article "Infrared Absorption Spectroscopy of Aqueous Solutions with a $CO_2$ Laser", *Applied Physics*, Magazine 7, pp. 287-293 (1975), the measurement sensitivity in infrared absorption tests using the transmission mode has been significantly improved by employing lasers with an essentially higher intensity than the previously known light sources. When lasers are used, however, there frequently occurs the undesired side effect of appreciable heating of the substance to be examined due to the strong absorption properties of aqueous solutions. This problem is rather easily met when testing aqueous solutions in inorganic materials available in ample amounts of solution. However, the tests are significantly more difficult if the same transmission measurements must be carried out for blood, which is available only in lesser amounts and which furthermore already denatures when heated to 45° C.

As was shown by applicant in an article in the book *Modern Techniques in Physiological Sciences*, Academic Press, London and New York, 1973, blood tests may also be carried out in vivo by means of laser beams. In that experiment, venous blood was passed in an extracorporeal shunt through a cuvette at a film thickness of 0.1 mm and at a flow rate of 30 cc per minute, and examined by means of a $CO_2$ laser beam of 2 watts. It was found that the temperature of the blood being tested could be kept below the critical temperature limit because of its high flow rate, and that $+/-0.5\%$ changes in concentrations in ethanol or glucose could readily be shown. However, this method suffers from the drawback that the examination is exceedingly costly and practically is suited only for large operation. This method furthermore suffers significantly from the problems of achieving even flow through very thin cuvettes and then cleansing of same.

Again the ATR (Attenuated Total Reflectance) method described by J. Fahrenfort in *Molecular Spectroscopy, Proceedings of a Conference at Brighton*, 1968, Elsevier Publishing Company, Amsterdam, pp. 111-130, has already been used. In this method, the radiation with which to examine a sample is so beamed into a suitable plate as to be totally reflected several times at oppositely located surfaces of this plate before being made to pass out of it and examined for changes in intensity. The sample to be tested touches one or both sides of the plate totally reflecting the beam.

SUMMARY OF THE INVENTION

The present invention now addresses the task of providing an instrument allowing rapid, simple and accurate indication of the amounts of metabolic products in the blood.

Starting with an instrument of the type initially mentioned, this problem is solved by the invention in that the radiation source is an infrared laser, and in that the laser radiation may be guided through an ATR plate into the boundary-surface region of which may be brought the blood containing the metabolic products.

Surprisingly it was found that such an arrangement for the first time permits an extremely sharp separation of the individual metabolic products which is the basic requirement for the quantitative determination of these individual products. For instance, as discussed in greater detail further below, the presence of contents in ethanol besides glucose can be unquestionably shown, which was impossible with spectrometers known previously.

Furthermore, this fact must be considered wholly surprising and revolutionary, namely that the instrument of the invention for the first time allows also determining the contents of metabolic products in the blood without at all removing this blood from the body. This may be achieved by placing the ATR plate directly against the skin and especially against the tongue. It was wholly surprising therefore that no difficulties due to tissue cell structure or overheating when locally applying laser beams were encountered in the quantitative measurements.

It was found that the power of the laser used is only limited by the degree of absorption of the ATR plate used.

The invention opens up wholly new feasibilities of examination and simplifies those already known. For instance, reliable serial tests for the early detection of diabetes can now be carried out for the first time. When testing for glucose under stress, the essential advantage is obtained that no blood need be taken at regular intervals from the patient.

Lasers that may be adjusted with respect to wavelength were found to be especially suitable. Semiconductor-diode lasers, parametric lasers and also gas lasers may be used. Parametric oscillators pumped by means of pulsed neodymium and tunable depending on the crystals from 1.4 to 4 microns (LiNbO$_3$) and from 1.22 to 8.5 microns (proustite) are particularly suitable.

Furthermore, both pulsed and continuous wave lasers may be used. Pulse-lasers offer the special advantage of introducing only minor stresses in the form of heating the blood being tested despite the high intensity available for such tests.

The angle of incidence of the laser beam with respect to the reflecting surfaces of the ATR plate are appropriately selected as the function of the ATR material. Preferably, however, they fall within the range of 45°–60°.

BRIEF DESCRIPTION OF THE DRAWINGS

The invention is explained below in greater detail, referring to the drawings, wherein.

DETAILED DESCRIPTION OF THE INVENTION

Figure 1:
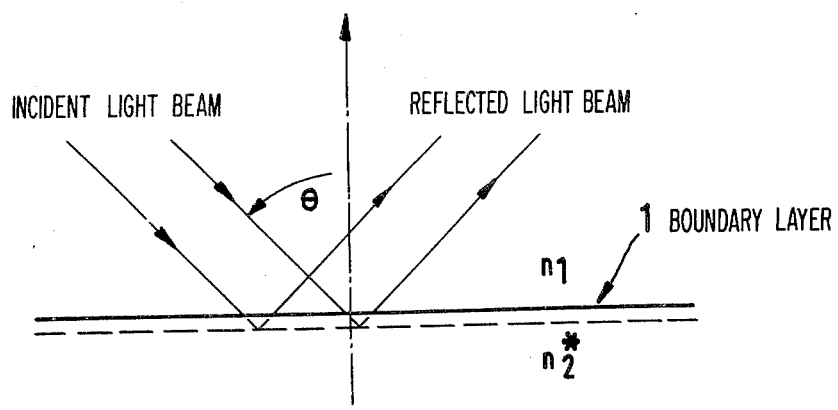
FIG. 1 is a diagrammatic representation of a total reflection process.

FIG. 1 merely shows diagrammatically the principle of total reflection, which occurs when the incident light from an optically denser material of index of refraction $n_1$ is incident on an optically less dense material of index of refraction $n_2^*$ at an angle $\theta$ exceeding the boundary total reflection angle obtained from the known laws of physical refraction. Essentially the total reflection phenomenon is characterized by no energy transfer taking place from the optically denser medium $n_1$ to the less denser optical medium $n_2^*$ ($n_1 > n_2^*$) on the average. The electromagnetic field, however, does spread in a narrow boundary layer in the less dense optical medium. If the less dense optical medium is not transparent, the equilibrium between the incident and reflected light energies is disturbed by radiation absorption in the boundary layer. This process is termed the so-called attenuated total reflection, or ATR. This damped total reflection is used for spectroscopic purposes with the ATR plate generally denoted by 2 and shown in FIG. 2.

Figure 2:
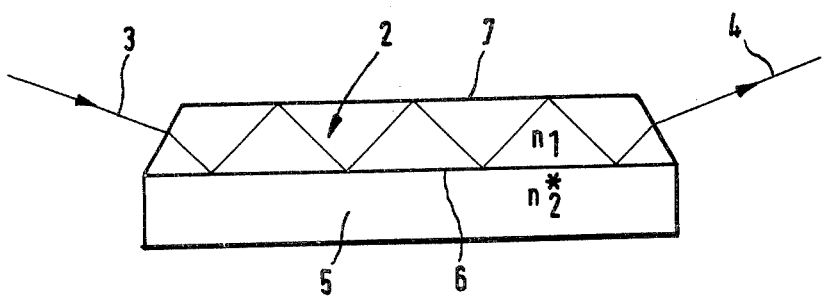
FIG. 2 is a diagram of an ATR plate.

This ATR plate 2 is shown in FIG. 2 is of essentially trapezoidal cross-section and has two opposite surfaces 6 and 7 which are essentially parallel to each other. Beam 3 used for testing is coupled into the plate by means of one of the trapezoidal end faces. The beam then is totally reflected several times at surfaces 6 and 7 before exiting at the opposite trapezoidal end face in the form of beam 4. The intensity of beam 4 exiting from plate 2 now may be affected by depositing the substance to be tested, which in this instance is schematically shown as 5, on one or both boundary surfaces 6 and 7, or by bringing it into contact with either or both.

The essential advantage in affecting beam 3 by the substance 5 to be tested consists in the latitude of arbitrarily selecting the layer thickness for all practical purposes without thereby influencing the result obtained, obeying merely the relation $d > 3\lambda$, where d is the layer thickness and $\lambda$ the wavelength of the test beam.

Several ATR plates for infrared spectroscopy already are known. Plates made from Geranium, Irtan 2, Irtan 6 or KRS 5 are preferred. The only essential feature for this procedure is that the particular ATR plate absorb as little as possible of the beam being used.

The information in beam 4 leaving the ATR plate is the higher, obviously, the larger the number of reflections taking place at the boundary layer touching the tested substance. On the other hand, the number of reflections clearly must be so chosen so that the signal obtained from beam 4 can be unambiguously measured and processed. ATR plates with dimensions 15 mm by 40–50 mm, and 1–2 mm thick, are used. The number of total reflections at the boundary layer with the tested substance was from 3 to 14. Good results are obtained when there were 5 total reflections at the boundary layer touching the tested substance.

Figure 3:
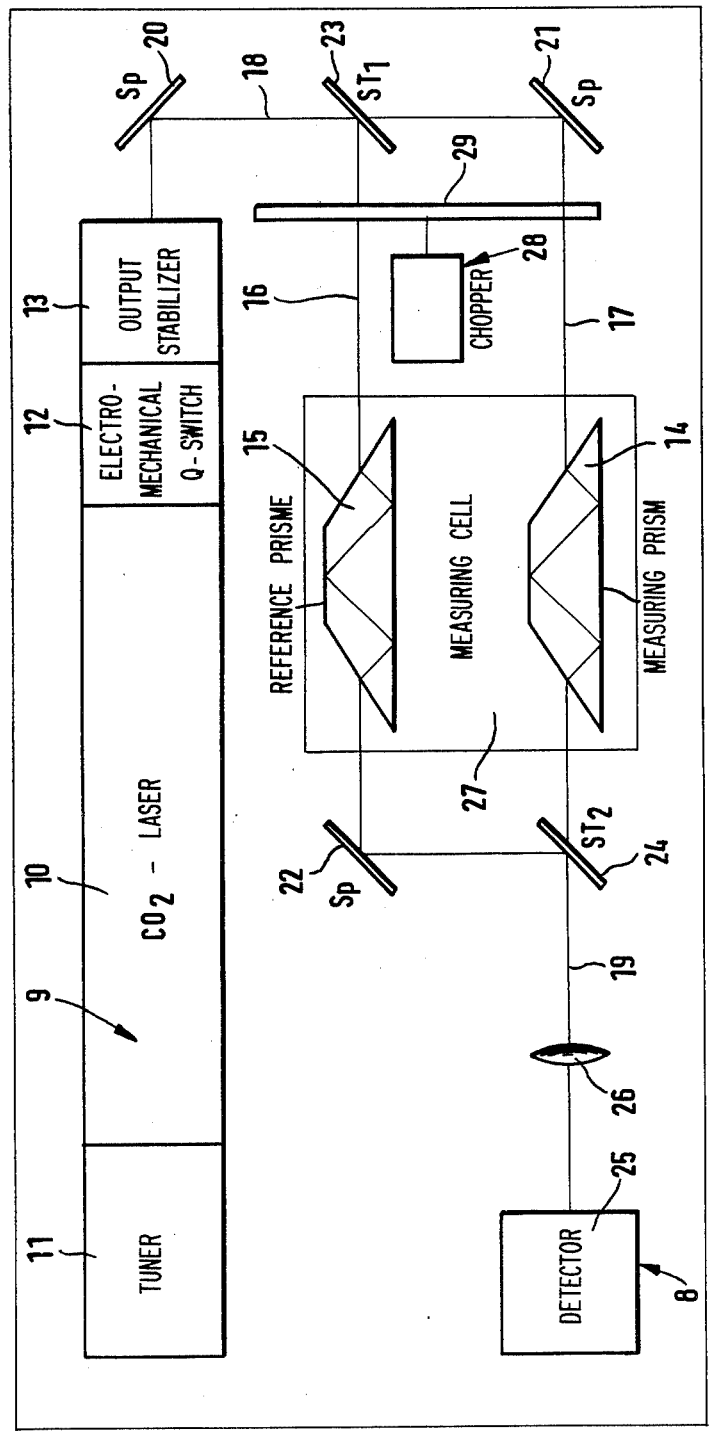
FIG. 3 is a diagrammatic illustration of an instrument constructed according to the invention.

FIG. 3 shows a diagrammatic embodiment of an instrument of the invention. In this instrument, as in conventional spectroscopy when measuring absorption, the method uses a reference beam. The radiation source is generally denoted by 9 in FIG. 3. This source consists of a laser 10, a tuning system 11 for the wavelength, an electronic Q-switch 12, and an output stabilizer 13.

A beam 18 generated by laser 10 is split by a semi-transmitting mirror into two half-beams 16 and 17 which are made to pass through the measurement cell 27, the latter containing an ATR measurement plate 14 and an ATR reference plate 15, both in the shape of prisms. The two half-beams 16 and 17 after exiting from the measurement cell are combined by means of mirrors 22 and 24 into a common beam 19 which then passes through a lens 26 and is incident on detector 25 of a signal processing system generally designated by 8.

In order to obtain higher sensitivity, the two half-beams 16 and 17 are chopped in a known manner by means of a chopper 28 comprising a chopper wheel 29. Chopper wheel 29 is provided with a varying sequence of apertures and stops on two different concentric circles so that the two half-beams 16 and 17 are converted into alternating light of relatively different frequencies. The frequency of rotation of a chopper motor can be varied in order to select the most favorable frequency range for the further processing of the signals obtained at detector 25.

Three types of detectors may be used in the spectral range of 10 microns: the photo-conductive Germanium semiconductor detectors Ge:Cu, Ge:Hg or Ge:Zn; the thermistors or pyroelectric triglycine-sulfate (TGS); or BaSr-Tio$_4$ based detectors. The processing of the signals obtained from detector 25 may be carried out in a known manner so that the potential $U_a(t)$ obtained at the output of the detector is split by two selective amplifiers in synchronism with the pertinent chopper frequencies $f_m$ and $f_r$ into the respective proportional potentials $U_m$ and $U_r$ corresponding to the light outputs $P_m$ of the reference beam and $P_r$ of the measuring beam.

A differential amplifier then forms $\Delta U = U_r - U_m$. If the conditions in the reference and measuring channels are the same, $\Delta U$ must be zero. Prior to each measurement, the control unit sets the null point by automatically balancing the differential amplifier. The difference in potential $\Delta U$ occuring during the measurement procedure is proportional to the difference in light power caused by the absorption of the measured medium, $$\Delta P = P_r = P_m.$$

Following the normalization $$\Delta U/U_r \sim \Delta P/P_r,$$

a signal will be available which is proportional to the absorption constant $\chi$ of the measured medium and hence to its concentration in the solution, for instance blood.

In principle, any infrared laser may be used, but frequency-tunable lasers are particularly advantageous. For the embodiment shown in FIG. 3, tests were carried out in particular with a 2 watt $CO_2$ laser and with a 5 watt model XB-5 by Apollo-Lasers, Inc. (USA). It was found in the course of the measurements that measurement accuracy is highly affected by the laser. In order to obtain high measurement accuracy, care must be paid to using a laser of high stability regarding frequency, mode and power. The aforesaid Apollo laser essentially meets these requirements.

The measurements carried out by means of the instrument described in FIG. 3 in principle involves deposition of the solution to be tested on one surface of the ATR measuring prism, while a control solution lacking the materials being tested—or in the case of blood, distilled water—was deposited on the corresponding surface of the ATR reference prism.

Figure 4:
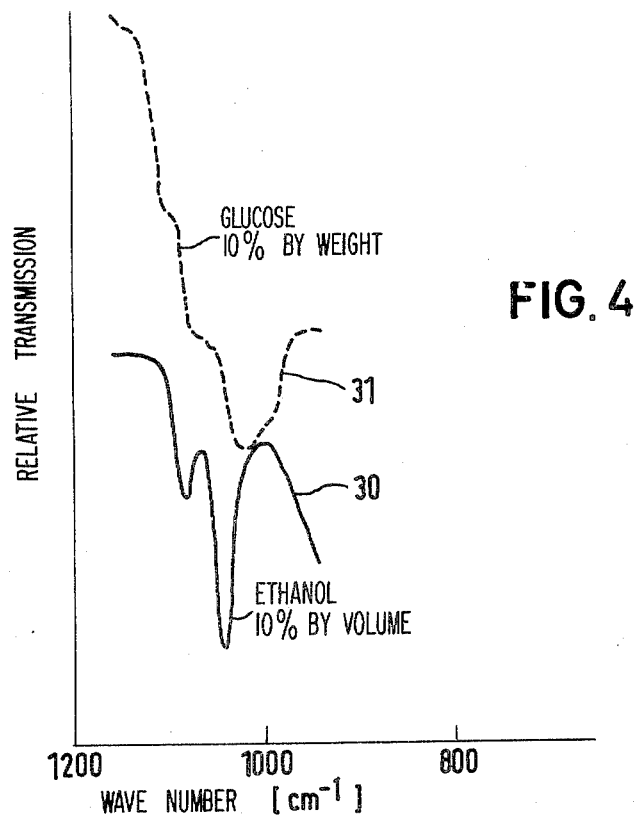
FIG. 4 shows the relative transmission as a function of the wavenumber for two different aqueous solutions, one containing 10% by weight of glucose and the other 10% by volume of ethanol, measured with a conventional spectrometer and on the same relative transmission scale.
Figure 5:
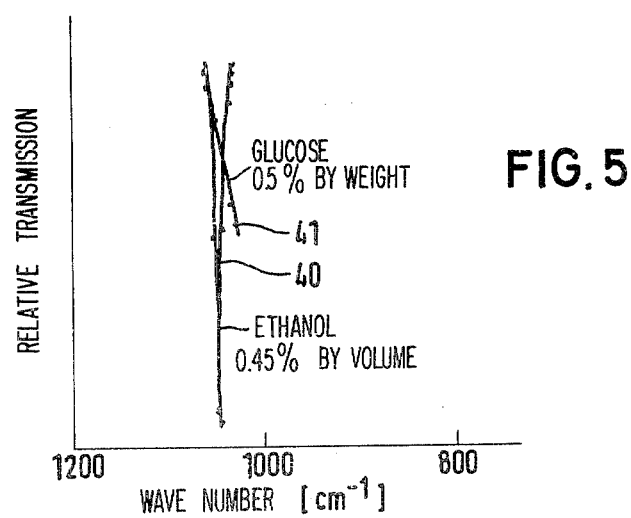
FIG. 5 shows the relative transmission as a function of wavenumber for two aqueous solutions, one with 0.45% by volume of ethanol and the other with 0.5% by weight of glucose, the measurements having been performed with an instrument of the invention.

The comparison between FIGS. 4 and 5 is merely intended to provide an example of the wholly unexpected capabilities of the instrument of the invention. The curves of FIGS. 4 and 5 are plotted on the same abscissa scale, the abscissa being in wavenumbers. FIG. 4 shows two different absorption curves, 30 and 31, recorded by means of one of the best previously conventional infrared spectrometers. The first curve, 30, shows the relative transmission of an aqueous solution containing 10% by volume of ethanol as a function of a wavenumber. The second curve, 31, shows the relative transmission of an aqueous solution containing 10% by weight of glucose. Both curves evidence a marked peak of absorption between the wavenumbers 1000 and 1050. The expert immediately sees that when measuring an aqueous solution simultaneously containing 10% by volume of ethanol and 10% by weight of glucose, the two absorption peaks can no longer be unambiguously distinguished, so that neither clear cut qualitative nor flawless quantitative conclusions would be possible from a corresponding absorption measurement.

FIG. 5 also shows two absorption curves, 40 and 41, in the same representation. Curve 40 shows the absorption curve of an aqueous solution containing 0.45% by volume of ethanol. Curve 41 shows an aqueous solution containing 0.5% by weight of glucose. The measurement of the glucose absorption curve unfortunately had to be terminated at a wavenumber slightly over 1000 because of being carried out with a $CO_2$ laser. However, the two curves clearly show that even in the presence of superposition of the curves, clearly separate evidence both of ethanol and of glucose is possible.

When measuring metabolic products in the blood, tests were performed in which the blood removed from the body was allowed to run over the measurement surface of ATR prism 14 or be let to dry, and also in which the ATR measurement prism 14 was made to lie with its boundary surface against the patient's tongue. In every case quantitative measurements of an accuracy of 5 mg% or 50 ppm. was obtained for metabolic products such as glucose, cholesterol and uric acid. These values were verified by corresponding measurements of conventional type. When using the aforesaid Apollo laser of especially stable characteristics, a further very significant increase in sensitivity was obtained, by means of which concentrations of 1 mg% ppm could be ascertained.

The invention has been described in respect to measuring the amounts of metabolic products in the blood. It is apparent that the invention may also be used similarly to measure minute impurities in aqueous solutions. This can also be applied to monitoring and controlling ecological pollution, including industrial waste waters and for monitoring and controlling industrial processes in general.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of determining the amounts of metabolic products in blood comprising the steps of placing an ATR plate against a living blood supplied living biological tissue, guiding a laser beam through said ATR plate, and detecting the intensity of said beam after being affected by the blood containing the metabolic elements.

2. The method as defined in claim 1 which includes the step of reflecting said beam from 2 to 14 times at the surface to the boundary region of which the blood is brought.

3. The method as defined in claim 1 wherein said laser beam has an angle of incidence from 45° to 60° with respect to the surface of the ATR plate at the boundary surface region of which the blood is brought.

4. The method as defined in claim 2 which includes the step of reflecting said beam from six to fourteen times at the surface to said boundary region.

5. The method as defined in claim 3 wherein said angle of incidence is about 50°.

6. A method of determining the amounts of metabolic products in blood comprising the steps of placing a first ATR plate against a surface of a living blood supplied being biological tissue and a second ATR plate against a reference solution lacking said metabolic products, splitting a laser beam from a single infrared laser into first and second partial beams of the same wavelength, guiding said first and second partial beams through said first and second ATR plates, respectively, and detecting the difference in intensity of said partial beams.

7. The method as defined in claim 6, wherein said reference solution is distilled water.

8. The method as defined in claim 6 which includes the steps of chopping said first and second partial beams into alternating light of different frequencies before said partial beams are guided through said ATR plates.

9. The method as defined in claim 8 which includes the step of recombining said partial beams into a single beam after passage through said ATR plates, said detecting step detecting the difference in intensities of the light at said different frequencies in said single beam.

* * * * *